(12) United States Patent
Teichmann et al.

(10) Patent No.: US 9,138,477 B2
(45) Date of Patent: Sep. 22, 2015

(54) USES FOR 4,17β-DIHYDROXYANDROST-4-ENE-3-ONE

(75) Inventors: Alexander Tobias Teichmann, Grossostheim (DE); Heinrich Wieland, St. Peter (DE)

(73) Assignee: MaBel GmbH, Erlangen (DE)

( * ) Notice: Subject to any disclaimer, the term of this patent is extended or adjusted under 35 U.S.C. 154(b) by 508 days.

(21) Appl. No.: 12/300,508

(22) PCT Filed: May 11, 2007

(86) PCT No.: PCT/EP2007/004220
§ 371 (c)(1),
(2), (4) Date: Nov. 12, 2008

(87) PCT Pub. No.: WO2007/131736
PCT Pub. Date: Nov. 22, 2007

(65) Prior Publication Data
US 2010/0061975 A1    Mar. 11, 2010

Related U.S. Application Data

(60) Provisional application No. 60/747,124, filed on May 12, 2006.

(30) Foreign Application Priority Data

May 12, 2006    (EP) ..................... 06009894

(51) Int. Cl.
*A61K 31/568* (2006.01)
*A61K 31/56* (2006.01)
*A61K 45/06* (2006.01)

(52) U.S. Cl.
CPC ............... *A61K 45/06* (2013.01); *A61K 31/568* (2013.01); *A61K 31/56* (2013.01)

(58) Field of Classification Search
CPC ............................ A61K 31/568; A61K 31/56
See application file for complete search history.

(56) References Cited

U.S. PATENT DOCUMENTS

| | | | |
|---|---|---|---|
| 2,744,120 | A | 5/1956 | Fried et al. |
| 2,762,818 | A | 9/1956 | Levy et al. |
| 4,235,893 | A | 11/1980 | Brodie et al. |
| 4,289,762 | A | 9/1981 | Metcalf et al. |
| 4,322,416 | A | 3/1982 | Metcalf et al. |
| 2003/0049307 | A1 | 3/2003 | Gyurik |
| 2003/0229063 | A1 | 12/2003 | Llewellyn |
| 2004/0018991 | A1 | 1/2004 | Schmidt et al. |
| 2004/0024231 | A1 | 2/2004 | Ring et al. |
| 2009/0111784 | A1 | 4/2009 | Teichmann |

FOREIGN PATENT DOCUMENTS

| | | | |
|---|---|---|---|
| BE | 552 152 | A | 11/1956 |
| BE | 552152 | A | 11/1956 |
| CA | 639855 | A | 4/1962 |
| EP | 0 100 566 | A1 | 2/1984 |
| EP | 0 307 135 | A1 | 3/1989 |
| GB | 2 100 601 | A | 1/1983 |
| GB | 2 398 495 | A | 8/2004 |
| JP | 2009-536932 | A | 10/2009 |
| WO | WO 01/23405 | A2 | 4/2001 |
| WO | 2005-014577 | A1 | 2/2005 |
| WO | 2005-034880 | A2 | 4/2005 |
| WO | WO 2005062760 | A2 | 7/2005 |
| WO | 2006-008639 | A1 | 1/2006 |

OTHER PUBLICATIONS

Leonard et al. Journal of the National Cancer Institute, 2004, vol. 96, No. 12, pp. 906-920.*
Pharm. Care & Res., Translated document, 2001, vol. 1, Issue 1, pp. 52-63.*
Bulk Nutrition, website www.bulknutrition.com, forum entry dated Feb. 5, 2004, Graham, NC, USA.
Office Action issued in corresponding Chinese Application No. 200780017205.9, issued Nov. 15, 2010.
Fu-Rong AN et al., "Aromatase Inhibitors in the Treatment of Breast Cancer," Pharm Care & Res. 2001, 1 (1), pp. 52-56.
Brodie et al., "Studies on the Mechanism of Estrogen Biosynthesis in the Rat Ovary-I," Journal of Steroid Biochemistry, 1976, vol. 7, pp. 787-793.
Covey et al., "A New Hypothesis Based on Suicide Substrate Inhibitor Studies for the Mechanism of Action of Aromatase," Cancer Research (Suppl.), vol. 42, pp. 3327s-3333s, Aug. 1982.
Goldenberg, Ira, S., "Testosterone Propionate Therapy in Breast Cancer," JAMA, vol. 188, No. 12, 1964, pp. 1069-1072.
Marsh et al., "Synthesis of Deuterium- and Tritium-Labeled 4-Hydroxy Androstene-3,17-Dione, An Aromatase Inhibitor, and Its Metabolism In Vitro and In Vivo in the Rat," Biochemical Pharmacology, vol. 31, No. 5, 1982, pp. 701-705.
Metcalf et al., "Substrate-Induced Inactivation of Aromatase by Allenic and Acetylenic Steroids," J. Am Chem. Soc., 103, 1981, pp. 3221-3222. (Abstract).
Ortmann et al., "Testosterone and 5 Alpha-Dihydrotestosterone Inhibit in Vitro Growth of Human Breast Cancer Cell Lines," Gynecol Endocrinol, Apr. 2002, 16 (2), pp. 113-120 (Abstract-Medline).
Szelei et al., "Androgen-Induced Inhibition of Proliferation in Human Breast Cancer MCF7 Cells Transfected With Androgen Receptor," Endocrinology, vol. 138, No. 4, 1997, pp. 1406-1412.
The Merck Index, 2001, Merck & Co., Whitehouse Station, NJ, XP002403136, p. 752.
International Search Report, issued in corresponding application No. PCT/EP2007/004220, completed Nov. 30, 2007, mailed Dec. 7, 2007.
Rote Liste (Red List), entries of 86 203 to 86 207.
Definition of "prophylactic", p. 1439 of Stedman's Medical Dictionary 26th edition, Williams & Wilkins, 1995, filed herewith as Exhibit A.

(Continued)

*Primary Examiner* — Samira Jean-Louis
(74) *Attorney, Agent, or Firm* — Griffin & Szipl, P.C.

(57) ABSTRACT

The present invention relates to novel uses of 4,17β-dihydroxyandrost-4-ene-3-one (hereinafter 4-hydroxytestosterone), to a process for their preparation, to pharmaceutical compositions containing them, and to the use of said compounds for the prophylaxis and/or treatment of breast cancer in mammals irrespective of the estrogen-receptor status of the tumor.

4 Claims, 3 Drawing Sheets

(56) References Cited

OTHER PUBLICATIONS

Wichmann, O. et al., "Prophylaxis Failure Due to Probable Mefloquine Resistant Resistant *P falciparum* From Tanzania, Department of Infectious Diseases and Tropical Medicine", University of Munich, Munich, Germany, Abstract of Acta Trop. Apr. 2003; 86(1): 63-5, filed herewith as Exhibit B.

Wei, CC et al., "Risk Factors for Prophylaxis Failure in Patients Receiving Aerosol Pentamidine for *Pneumocystis carinii* Pneumonia Prophylaxis", Department of Medicine, University Health Network and Mount Sinai Hospital, Toronto, Ontario, Canada, Abstract of Chest. May 2001; 119(5): 1427-33, filed herewith as Exhibit C.

Dunner, DL, "Lithium Carbonate Prophylaxis Failure", Abstract of Br J Psychiatry. Jul. 1976; 129: 40-4, filed herewith as Exhibit D.

Hughes, D., "Exemastane Significantly Reduces Risk of Invasive, Preinvasive Breast Cancers in Postmenopausal Women at High Risk", webpage http://www.empr.com/exemestane-significantly-reduces-risk-of-invasive-preinvasive-breast-cancers-in-postmenopausal-women-at-high-risk/article/204502/, pp. 2-4, Jun. 4, 2011, filed herewith as Exhibit E.

Raynaud, JP, et al., "Screening for Anti-Hormones by Receptor Studies", Journal of Steroid Biochemistry, 6: 615-622 (1975) (Abstract Popline).

Office Action mailed Jul. 11, 2011 in corresponding European Application No. 07725141.1.

Hu, et al., Androgen Receptor Expression and Breast Cancer Survival in Postmenopausal Women, Clin. Cancer Res., 17(7), 2011, pp. 1867-1874.

Ortmann, et al., "Testosterone and 5 alpha-dihydrotestosterone Inhibit in Vitro Growth of Human Breast Cancer Cell Lines" Gynecol. Endocrinol., 16(2), 2002, pp. 113-120.

Office Action issued on Jul. 30, 2012 and mailed on Aug. 6, 2012 relating to JP Application No. 2009-508259.

Brueggemeier, Robert W., et al. "Aromatase Inhibitors in the Treatment of Breast Cancer," Endocrine Reviews 26 (3):331-345, 2005.

Office Action issued in co-pending Korean application 10-2008-7027501 on Aug. 22, 2013.

Office Action isssued in co-pending Korean application 10-2008-7027498 on Aug. 22, 2013.

Office Action issued in co-pending related U.S. Appl. No. 12/300,503 on Feb. 14, 2014.

Kohler et al., Metabolism of 4-hydroxyandrostenedione and 4-hydroxytestosterone: Mass spectrometric identification of urinary metabolites, 72 Steroids 278-286 (2007), which has been filed in a related application as "Exhibit A2.".

Kadohama et al., Kinetic properties of aromatase mutants Pro308Phe, Asp309Asn, and Asp309Ala and their interactions with aromatase inhibitors, 43 J Steroid Biochem Mol Biol. 693-701 (1992), which has been filed in a related application as "Exhibit A3.".

Marsh et al., Synthesis of deuterium- and tritium-labelled 4-hydroxyandrostene-3,17-dione, an aromatase inhibitor, and its metabolism in vitro and in vivo in the rat, 31 Biochem Pharmacol. 701-5 (1982), which has been filed in a related application as "Exhibit A4," pp. 701-705.

Brodie, Aromatase inhibitors and models of breast cancer, Birkhäuser Monograph, Aromatse Inhibitors, ed. J.A. Furr, (2006), which has been filed in a related application as "Exhibit A5", pp. 23-44.

Hu et al., Androgen Receptor Expression and Breast Cancer Survival in Postmenopausal Women, 17 Clin. Cancer Res. 1867-1874 (2011), which has been filed in a related application as "Exhibit A6.".

A research study conducted by Cerep, a French independent contract research organization, Jul. 5, 2010, which has been filed in a related application as "Exhibit A7.".

A research study conducted by the in vitro—Institut für Molekularbiologie, a German independent contract research organization, which has been filed in a related application as "Exhibit A8," 2012, pp. 1-28.

A research study conducted by a study by Deutsche Sporthochschule Cologne, Germany, which has been filed in a related application as "Exhibit A9," 2008, pp. 1-7.

Stedman'S Medical Dictionary 1099, 1100, 1588 and 1871 (1995).

"Facts for Life, Prognostic Factors," Susan G. Komen for the Cure (2010), which has been filed in a related application as Exhibit B1. http://www.breastcancer.org/treatment/hormonal/aromatase_inhibitors/ (downloaded Oct. 11, 2012).

* cited by examiner

Fig. 1C

USES FOR 4,17β-DIHYDROXYANDROST-4-ENE-3-ONE

This is a National Phase Application in the United States of International Patent Application No. PCT/EP2007/004220 filed May 11, 2007, which claims priority on European Patent Application No. 06 009 894.4, filed May 12, 2006 and U.S. Provisional Application No. 60/747,124, filed May 12, 2006. The entire disclosures of the above patent applications are hereby incorporated by reference.

The present invention relates to novel uses of 4,17β-dihydroxyandrost-4-ene-3-one (hereinafter 4-hydroxytestosterone) and its salts and esters, to a process for their preparation, to pharmaceutical compositions containing them, and to the use of said compounds for the prophylaxis and treatment of certain diseases in mammals, in particular cancers.

After colorectal cancer breast cancer is the most frequent cancer disease in the western world despite the fact that it affects almost exclusively women. In Germany, breast cancer amounts to about 20% of all cancer types diagnosed in women. The therapy in most of the cases consists of surgical removal of the tumour (lumpectomy) or complete removal of the affected breast if the size of the tumor prevents breast conserving therapy. In both cases the operation is followed by drug therapy. A particular complication of breast carcinomas is the high potential of metastatic spread into other organs particularly liver, brain, bones and the skin. Therefore the operation is followed by drug therapy (adjuvant therapy). This therapy is also aimed at preventing local recurrence of the disease.

If the removed tumours were exhibiting estrogen receptors, antiestrogens are used (Tamoxifen or aromatase-inhibitors). The lack of estrogen receptors leads to a postoperative drug therapy using cytostatic drugs.

Tamoxifen binds to the estrogen receptor (ER) and blocks the growth promoting effect of estrogens. Aromatase-inhibitors block the final step in the production of estrogens from androgenic precursors (c-19-steroids). They either bind irreversibly to the active site of the enzyme (aromatase-inactivators, i.e. steroidal aromatase-inhibitors: 4-hydroxyandrostenedione (Formestane=Lentaron®), or Exemestane (Aromasin®)) or inhibit competitively the cytochrome p 450 part of the enzyme (nonsteroidal aromatase-inhibitors: Anastrozol (Arimidex®) and Letrozol (Femara®).

If the breast cancer exhibited an overexpression of the Her2neu gene, antibodies against this cell-surface protein are given intravenously such as e.g. Trastuzumab (Herceptin®).

Basic and clinical data indicate that aromatized metabolites of androgens, i.e. the estrogens, are the hormones involved in the pathogenic cellular changes associated with the growth of some hormone-dependent cancers, such as breast, endometrial and ovarian carcinomas. Aromatase has recently been recognized as an enzyme that is capable to synthesize estradiol directly in tumours.

Endogenous estrogens are ultimately formed from either androstenedione or testosterone as immediate precursors. The local production of estrogens in the breast tissue, especially in the tumour cells itself, had been regarded to be of great importance for the therapy of the disease. In this context, aromatization of the steroidic ring A performed by the enzyme aromatase, and its inhibition had been considered to play a major role in anti breast cancer approaches.

Prior to the present invention, conventional therapeutic approaches to address breast cancer in women—besides other concepts based on estrogen receptor antagonists or therapeutic antibodies—therefore focused on an aromatase-inhibiting action itself. Accordingly, steroidal substances which had been reported to be endowed with an aromatase-inhibiting action have been described, for example $\Delta^1$-testololactone [U.S. Pat. No. 2,744,120], 4-hydroxy-androst-4-ene-3,17-dione and esters thereof [see, for example, U.S. Pat. No. 4,235,893], 10-(1,2-propadienyl)-estr-4-ene-3,17-dione (U.S. Pat. No. 4,289,762], 10-(2-propynyl)-estr-4-ene-3,17-dione [J. Amer. Chem. Soc., 103, 3221 (1981) and U.S. Pat. No. 4,322,416], 19-thioandrostene derivatives (Europ. Pat. Appl. 100566), androsta-4,6-diene-3,17-dione, androsta-1,4,6-triene-3,17-dione [G.B. Pat Appl. 2,100,601A] and androsta-1,4-diene-3,17-dione [Cancer Res. (Suppl.) 42, 3327 (1982)].

Clinical studies conducted with estrogen-receptor (ER) antagonists and aromatase inhibitors however showed that these compounds were not able to exert a significant and sufficient inhibitory effect on tumour proliferation and/or growth. For example, Tamoxifen® based therapy suffers from drawbacks such as tachyphylaxy (therapy failure) and the fact that its effects in some cells are estrogen-like (e.g. risk for thrombosis and edometrial cancer) being the reason that Tamoxifen® can not be administered for a period longer than 3 to 5 years. Newer drugs such as aromatase inhibitors can in principle only be used in post-menopausal women and, furthermore, are only effective on ER-positive tumours.

It could be shown (J. Szelei et al., "Androgen-Induced Inhibition of Proliferation in Human Breast Cancer MCF7 Cells Transfected with Androgen Receptor", Endocrinol., 138, no. 4, 1406-1412, 1997) that stable transfected cells expressing AR acquire the ability to respond to androgen by evoking an end of cellular proliferation. A more recent report (J. Ortmann et al., "Testosterone and 5α-dihydrotestosterone inhibit in vitro growth of human breast cancer cell lines", Gynecol. Endocrinol. 2002; 16:113-120) shows that testosterone and 5α-dihydrotestosterone (DHT) can inhibit cell proliferation in certain cell lines. Testosterone itself has a similar effect. Its clinical usefulness however is hampered by the fact that it undergoes rapid metabolization to either estradiol or dihydrotestosterone (DHT). The local formation of estradiol from testosterone within the breast cancer by local aromatase activity promotes cancer-growth.

Thus, there is a high demand for alternative androgen-receptor (AR) specific compounds that exert testosterone-like effects (in particular anabolic effects) in AR-positive cells and tissues and are not metabolized by aromatase or transformed to DHT by 5-alpha-reductase.

According to the present invention, therapeutic efficacy of 4,17β-dihydroxyandrost-4-ene-3-one has been discovered in a surprising new context, enabling valuable medical applications. As a result, the present invention involves the use of 4,17β-dihydroxyandrost-4-ene-3-one or its salts or esters for prophylaxis against or the treatment of breast cancer (in particular ductal, medullary and lobular breast carcinoma), endometrial carcinoma, cervix carcinoma, epithelial ovarian carcinoma, uterine (fallopian) carcinoma, benign proliferative change or alteration of the breast, fibroadenoma, macromastia (peri-postmenopausal), mastopathy, myoma, and secondary or metastatic tumors derived therefrom.

"Use" according to the present invention may include method of treatment or prophylaxis of the specified compounds, or of a pharmaceutical composition containing the same as an active principle together with a suitable carrier and/or diluent, for the mentioned indications, and it includes use in the preparation of said pharmaceutical composition.

Based on the findings in the present invention, 4,17β-dihydroxyandrost-4-ene-3-one is particularly suitable for prophylaxis against and/or treatment of breast cancer in female or male patients.

The pharmaceutical composition according to the present invention may further contain (an) effective amount(s) of (an) estrogen-receptor antagonist(s) and/or aromatase inhibitor(s) (a compound different from the compounds of the invention disclosed herein), and/or cytostatic(s) and/or antibodies against Her2neu.

Since the compounds according to the present invention can most effectively exert their effects directly at the target cells or target tissue, without systemically affecting the treated patient, the pharmaceutical composition according to the present invention is preferably formulated for topic administration for local treatment at the target site to be treated.

The compounds of the present invention exhibit androgen-receptor (AR) binding affinity. In most cells, except breast cancer cells they are capable of inducing an anabolic effect, provided they exhibit AR. In breast cancer cells they induce apoptosis.

These compounds are neither substrates for nor metabolic products from aromatase and thus do not share the negative effects of substances being metabolized by aromatase. Furthermore, the compounds of the present invention are not substrates for 5α-reductase. As these substances cannot be that easily metabolised as, for example, testosterone, their inhibitory effect on the tumour cell is greatly facilitated and they additionally exert an apoptotic effect on the tumour cell itself. Therefore, these substances are presumably more efficient in the treatment of breast cancer cells than the line of currently used substances to treat both types of breast cancer. Another beneficial effect of this prophylactic or therapeutic concept is that even in estrogen receptor negative (ER-negative) tumours there is a high probability of the cells to be AR-positive and therefore even these tumours currently treated only with cytostatic drugs can be pharmacologically addressed by 4-hydroxytestosterone, thereby increasing the range of hormonal breast cancer therapy significantly.

Since the compounds of the present invention are AR specific compounds, but are not metabolized by aromatase, they can fully exert their actions and effects associated with the specifically defined therapeutic or prophylactic uses via AR. This makes the concept of the presently selected compounds distinct over the prior art. It also explains the basic difference over previous therapeutic uses of 4-hydroxytestosterone or its derivatives. In particular, a disclosure of U.S. Pat. No. 2,762, 818A does not go beyond using 4-hydroxytestosterone and its esters to treat an androgen deficiency status itself based on their androgenic and anabolic properties. There was however neither a purpose nor a finding which would suggest an activity on breast cancer cells or on effects from which an efficacy against the disease conditions according to the present invention could have been deduced. Further, US2003/0229063A addresses low androgen to estrogen ratios in men (leading to endocrine disorders) and only for this purpose attempts to make use of 4-hydroxytestosterone based on an asserted aromatase-inhibiting effect alone.

In experiments carried out with the compounds of the present invention it could be shown that these substances had excellent skin penetration capabilities so that a sufficient influence on tumour growth (up to apoptosis) could be achieved by simple topic administration of e.g. an ointment, lotion or cream etc. comprising a therapeutically or prophylactically effective amount of a compound according to the present invention to an area of a patient in need of treatment. After topical administration, the compound(s) penetrate through the skin and concentrate in the subcutaneous adipose tissue.

In the case of breast cancer, the medicament can be applied locally to the skin of the breast, such that the preferably strongly lipophilic active compound is transdermally absorbed and thus brought locally to the intended site of action. The active compound concentrates in the periductal fatty tissue. In a long-term treatment, the fatty matter of the treated breast is markedly reduced. This reduction decreases the quantity of oestrogen-forming cells having oestrogen-forming competence. The lipophilicity and hydrophobicity of the active compound has the result that the active compound is exclusively concentrated locally in the fatty tissue and thus cannot display any significant systemic action.

According to a preferred embodiment of the present invention it is intended to apply the medicament topically immediately on or in the vicinity of the intended site of action. According to the invention, the result achieved is an adequate local active compound level in the tissue at risk (in prophylaxis) or in the diseased tissue (in therapy) without a noticeable absorption of the active compound taking place in the blood circulation. The benefit of this embodiment thus not only relies in the topical application per se, but in the local topical application in such a way that the active compound concentrates strongly in the tissue at risk and/or diseased tissue, and not indirectly via the blood circulation.

Owing to the primary target disease to be treated as described above, especially for breast cancer etc., a local topic treatment or prophylactic application is predominantly carried out with female patients and particularly on breast skin of female patients, although the same therapeutic principle applies also to male breast cancer.

If metastasizing carcinomas are also to be treated and/or prophylaxis is to be carried out against these, the medicament according to the invention can be applied topically to the intended site of action in such an amount that a noticeable absorption in the blood circulation additionally takes place and a serum level thus builds up which also transports the active compound to metastases. In this use too, a local absorption on or in the vicinity of the intended site of action, notably where metastasizing carcinomas exist, also primarily takes place.

An important advantage of the invention is the possibility of also using the medicament for breast cancer prophylaxis. A particularly advantageous possibility of employment is so-called secondary prophylaxis. In female or male patients in whom a breast cancer has been diagnosed and treated, there is a certain risk of recurrence at the same site and also a high risk of a further carcinoma in the contralateral breast. In both cases the endowment of the second cancer with ER is not predictable. The operated and the contralateral breast can then be treated prophylactically with the medicament according to the invention. It will prevent also the appearance of a ER negative cancer (particularly common in patients suffering from a familiar predisposition for breast cancer).

In the case of so-called high-risk women, primary prophylaxis can be performed. The selection criteria which can be used for such a high-risk group are, for example, the facts that at least one female or male relative of first degree on the mother's side is or has been suffering from breast cancer on one side before the 45th year of life or bilaterally, or that on the mother's side at least one female or male relative of first degree and an additional female or male relative are or have been suffering from breast cancer.

In the majority of theses cases the underlying cause of the disease is a genetic defect in one of the two known "breast cancer genes" BRCA1 and BRCA2.

Since the local application according to a preferred embodiment of the invention virtually completely avoids possible systemic side effects of the active compound on account of its hydrophobicity and high safety profile, the indication for primary prophylaxis can be made relatively generously already in the presence of tissue having a comparatively low or average risk. Prophylaxis can be started long time before signs and symptoms of breast cancer may be occurring.

In the preferred topical administration the compound or composition according to the invention is preferably applied over a relatively long period of time (if needed up to lifelong) and application is carried out, for example, once or twice per day. Since the active substances of the invention intended to be applied topically (locally) are preferably provided in lipid-soluble form, they can easily penetrate into the fatty tissue and locally exert their prophylactic and/or therapeutic effect.

Since the active compounds administered topically according to the invention remain localized in the fatty tissue of the breast and display their intended action there on account of their lipid solubility, any possible side effects induced by systemic application are eliminated. This reduction or exclusion of side effects allows significantly wider prophylactic use. The medicament according to the invention can be applied by patients themselves and frequent visits to the doctor for this purpose are not necessary.

As a rule for topic administration, the active compounds used according to the invention are lipid-soluble and highly suitable for topical application. As already described above, the concentration in the fatty tissue of the breast avoids systemic side effects. To improve the skin penetration, substances known in the prior art which promote this can be added to the medicament according to the invention, for example hyaluronidases, Dimethylsorbitol or DMSO (dimethyl sulphoxide).

In particular, the topic administration is mainly indicated for primary prevention (prophylaxis), secondary prevention (prophylaxis) after breast conserving therapy, accompanied by any form of adjuvant drug therapy, after operation for 'ductal carcinoma in situ' (DCIS, which is usually not followed by any adjuvant therapy) and prophylaxis of contralateral breast cancer. The topic administration is also particularly suited in the context of 'neoadjuvant' therapy. This implies the drug treatment of the cancer before operation in order to diminish its size to allow for breast conserving operation. In the past this has been done preferentially in cases of ER-negative tumors, only recently aromatase inhibitors have been used with limited success within 6 months. Finally the treatment can be applied to superficial lesions (e.g. cutaneous metastases)

Primary prevention relates to the prophylactic treatment of healthy individuals bearing a certain risk to develop cancer. Since the compounds and pharmaceutical compositions of the invention are not a substrate of aromatase and thus cannot be metabolized to estrogens, and are not virilizing, they can also be used in the primary prevention of breast cancer in premenopausal women. In secondary prevention, the compounds and compositions may be used alone or in combination with e.g. Tamoxifen, aromatase inhibitors, herceptine and/or cytostatic drugs, wherein any of such combinations would enlarge the spectrum of treatable cell types.

The present invention is based on the findings that 4,17β-dihydroxyandrost-4-ene-3-one (hereinafter 4-hydroxytestosterone) can successfully be used as a pharmaceutically active substance. In particular, it could be shown that pharmaceutical compositions containing a suitable carrier and/or diluent and, as an active principle, 4-hydroxytestosterone, can be used in the prophylaxis and/or treatment of breast cancer (in particular ductal, medullary and lobular breast carcinoma), endometrial carcinoma, cervix carcinoma, epithelial ovarian carcinoma, uterine (fallopian) carcinoma, benign proliferative change or alteration of the breast, fibroadenoma, macromastia (peri-postmenopausal), mastopathy, myoma, and secondary or metastatic tumors derived therefrom.

Hence, the present invention likewise provides the use of 4,17β-dihydroxyandrost-4-ene-3-one (4-hydroxytestosterone) in the preparation of a pharmaceutical composition for the (clinical) prophylaxis and/or treatment of the above hormone-dependent or hormone receptor regulated cancers in mammals.

In general, the compounds and pharmaceutical preparations of the invention can be administered topically, orally, rectally, parenterally (e.g. intramuscularly or by intravenous injection or infusion), transdermally and/or in the form of a depot preparation.

The compound of the present invention, 4-hydroxytestosterone, is disclosed in e.g. U.S. Pat. No. 2,762,818 A and commercially available (e.g. from Bulk Nutrition, Graham, N.C., USA; see bulknutrition.com for further information; WINKOS GmbH D-79189 Bad Krozingen, DE).

The present invention also pertains to all derivatives (in particular salts and esters of 4,17β-dihydroxyandrost-4-ene-3-one that share its functional and/or structural features. Examples of suitable ester groups include, but are not limited to straight chain, branched chain or cyclic or aromatic acyl groups, such as formyl, acetyl, propionyl, butyryl, pentanoyl, hexanoyl, heptanoyl and benzoyl. The esters can be formed with the 4 and/or 17 hydroxy group, preferably with the 17 hydroxy group. Its salts and esters can also be prepared by known methods (see e.g. U.S. Pat. No. 2,762,818 A).

The compounds and pharmaceutical preparations of the invention are anabolic steroids and exert their testosterone-like effects upon binding to androgen receptors displayed in cells and tissues being AR-positive.

In view of their high therapeutic index, the compounds of the invention can be used safely in medicine. For example, the approximate acute toxicity ($LD_{50}$) of the compounds of the invention in the mouse, determined by single administration of increasing doses and measured on the seventh day after the treatment was found to be negligible.

The compounds and pharmaceutical preparations or compositions of the invention can be administered in a variety of dosage forms, e.g. topically, in the form of an ointment, a cream, a lotion, a gel, a spray, or a transdermal plaster, also comprising depot dosage forms (including pellets), orally, in the form of tablets, capsules, sugar or film coated tablets, liquid solutions or suspensions: rectally, in the form of suppositories; parenterally, e.g. intramuscularly, or by intravenous injection or infusion.

According to a preferred embodiment, the compounds of the invention are designed for topical administration.

The dosage depends on the age, weight, conditions of the patient and administration route; for example the dosage adopted for oral administration to adult humans may range from about 10 to about 150-1000 mg pro dose, from 1 to 5 times daily.

The invention includes pharmaceutical preparations or compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For topical administration, the medicament is preferably formulated as an ointment, cream, gel, emulsion or lotion. Formulation as a powder or oil is also conceivable. Formulation bases are familiar to the person skilled in the art from the cosmetic and pharmaceutical industry and do not need to be explained here in greater detail. For example, vegetable oils and fats such as almond oil, peanut oil, olive oil, peach kernel oil, castor oil, plant extracts, ethereal oils; furthermore vegetable waxes and synthetic and animal oils, fats or waxes; lecithin, lanolin alcohols, carotene, fragrances, mono- or polyhydric alcohols, urea, preservatives and colourants etc. can be used. Formulation as an oil-in-water or water-in-oil emulsion is preferred.

The active compound content of a suitable medicament can be between 0.0001 and 20% by weight, preferably 0.6% until 10% by weight, further preferably 1 and 5% by weight, of 4-hydroxytestosterone or its salts or esters. A customary range is 0.6 to 5% by weight.

If substances are admixed to promote skin penetration, their content, when using hyaluronidases, can be, for example, between 0.01 anti 1% by weight, preferably 0.05 anti 0.2% by weight, when using dimethylsorbitol or DMSO between 1 and 25% by weight, preferably 5 and 10% by weight.

For example the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatine, methylcellulose, carboxymethylcellulose or polyvinyl pyrrolidone; disaggregating agents, e.g. a starch, alginic acid, alginates or sodium starch glycolate; effervescing mixtures; dyestuffs, sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

In cases where the target tumour is estrogen-receptor (ER) positive, the compounds of the invention can also be administered together with known estrogen-receptor antagonists (such as Tamoxifen®) and/or known aromatase inhibitors and/or known cytostatics. Thus, a pharmaceutical composition of the invention may also comprise an effective amount of (a) known compound(s) exerting estrogen-receptor antagonistic and/or aromatase inhibitory activity and/or cytostatic activity. According to a preferred embodiment, a combination of 4-hydroxytestosterone and a suitable cytostatic or combination of cytostatics is provided, in particular, in form of a preparation that can be administered topically (e.g. cream).

Examples of suitable aromatase inhibitors are e.g. disclosed in US 2004/0018991 A1 and include steroidal aromatase inhibitors such as formestane and lentaron, exemestane, MDL 18962, 7 alpha-substituted androstenedione derivatives, ATD, 10-oxirane and 10-thiirane-substituted androgens, atamestan, etc., and non-steroidal aromatase inhibitors such as vorazol, arimidex, letrozol, fadrozol, and rogletimid. With regard to the designations of these substances as well as their availability, see for example "Red List", Editio Cantor, Aulendorf (DE, 1999).

Examples of suitable cytostatics and cytostatic combinations include e.g. AC±T—Adriamycin (chemical name: doxorubicin) with cyclophosphamide (brand name: Cytoxan), with or without Taxol (chemical name: paclitaxel) or Taxotere (chemical name: docetaxol); CMF—cyclophosphamide, methotrexate, and fluorouracil ("5-FU" or 5-fluorouracil); CAF—cyclophosphamide, Adriamycin, and fluorouracil ("5-FU" or 5-fluorouracil); CEF—cyclophosphamide, Epirubicin (similar to Adriamycin), and fluorouracil ("5-FU" or 5-fluorouracil); FAC—fluorouracil ("5-FU" or 5-fluorouracil), Adriamycin, and cyclophosphamide.

In general, and in particular if the target tissue is estrogen-receptor negative, the compounds of the invention can also be administered together with antibodies against Her2neu such as e.g. Trastuzumab (Herceptin®)). Thus, a pharmaceutical composition of the invention may also comprise an effective amount of known compounds exerting antagonistic Her2neu activity.

The following examples illustrate but do not limit the invention.

Example 1

The compound of the present invention can be synthesized as follows.

In a first step, 2.5 g testosterone is dissolved in 100 ml cold MeOH. After adding 9 ml NaOH (2%) and 17 ml $H_2O_2$ (30%) the mixture is stirred for 24 h at 4° C. The resulting epoxids are precipitated with ice-water.

In a second step, 2 g of the dry epoxids are dissolved in 200 ml acetic acid containing 2% $H_2SO_4$. The solution is stirred for 4 h at room temperature. The reaction products are precipitated with ice-water.

Thereafter, the reaction products are washed with 1% NaOH solution to hydrolyse the acetyl esters. The total yield of pure 4-hydroxytestosterone is in the range of 40-50%.

Example 2

A cream for topical administration according to the invention can be formulated in conventional manner using the following amounts of ingredients. The amounts are given per 100 g of cream:

| | |
|---|---|
| 4-hydroxy-17β-acetyl-androst-4-en-3-one | 4.5 g |
| Cetearyl alcohol | 7.5 g |
| Paraffin wax | 3.0 g |
| Sodium carbomer | 2.5 g |
| Isopropyl myristate | 6.0 g |
| Sorbitan monostearate | 1.0 g |
| Polysorbate 20 | 3.0 g |
| Stearyl alcohol | 2.0 g |
| Dimethylsorbitol | 5.0 |
| Purified water qs | 100.0 g |

The resulting cream can be given topically on the skin above affected breast tissue of a female or male patient.

Example 3

A gel according to the invention can be formulated in conventional manner using the following amounts of ingredients. The amounts are given per 100 g of gel:

| | |
|---|---|
| 4-hydroxytestosterone | 2.5 g |
| Ethanol 95.degree | 70.0 g |
| Carbopol 980 | 0.5 g |
| Isopropyl myristate | 2.5 g |
| Triethanolamine | 0.5 g |
| Purified water qs | 100.0 g |

Example 4

A solution for use as a spray according to the invention is prepared in conventional manner using the following formulation. The amounts are given per 100 g of solution:

| | |
|---|---|
| 4-hydroxytestosterone | 2.5 g |
| Ethanol 95.degree. | 70.0 g |
| Isopropyl myristate | 2.5 g |
| Purified water qs | 100.0 g |

Example 5

Tablets each weighing 0.150 g and containing 25 mg of the active substance, can be manufactured as follows:
Composition (for 10000 tablets)

| | |
|---|---|
| 4,17β-dihydroxyandrost-4-ene-3-one | 250 g |
| Lactose | 800 g |
| Corn starch | 415 g |
| Talc Powder | 30 g |
| Magnesium stearate | 5 g |

The 4,17β-dihydroxyandrost-4-ene-3-one, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

Example 6

Capsules, each dosed at 0.200 g and containing 20 mg of the active substance can be prepared.

Composition for 500 capsules:

| | |
|---|---|
| 4,17β-dihydroxyandrost-4-ene-3-one | 10 g |
| Lactose | 80 g |
| Corn starch | 5 g |
| Magnesium stearate | 5 g |

This formulation is encapsulated in two-piece hard gelatine capsules and dosed at 0.200 g for each capsule.

Example 7

MCF-7 cells were grown in RPMI 1640 medium at 37° C. to a cell number of about $1*10^5$ cells/ml. Then, in quadruple identical MCF-7 cell samples, there were added either dihydrotestosterone (DHT) or 4-hydroxytestosterone (4-OHT), to obtain different concentrations thereof, namely $10^{-7}$ M, $10^{-8}$ M or $10^{-9}$ M, and further growth of cells were determined by counting of vital cells. During the course of incubation at 37° C., cell counting were performed after 3, 6 and 9 days. For control, growth of MCF-7 cells were determined without addition of an active agent.

Figure 1:
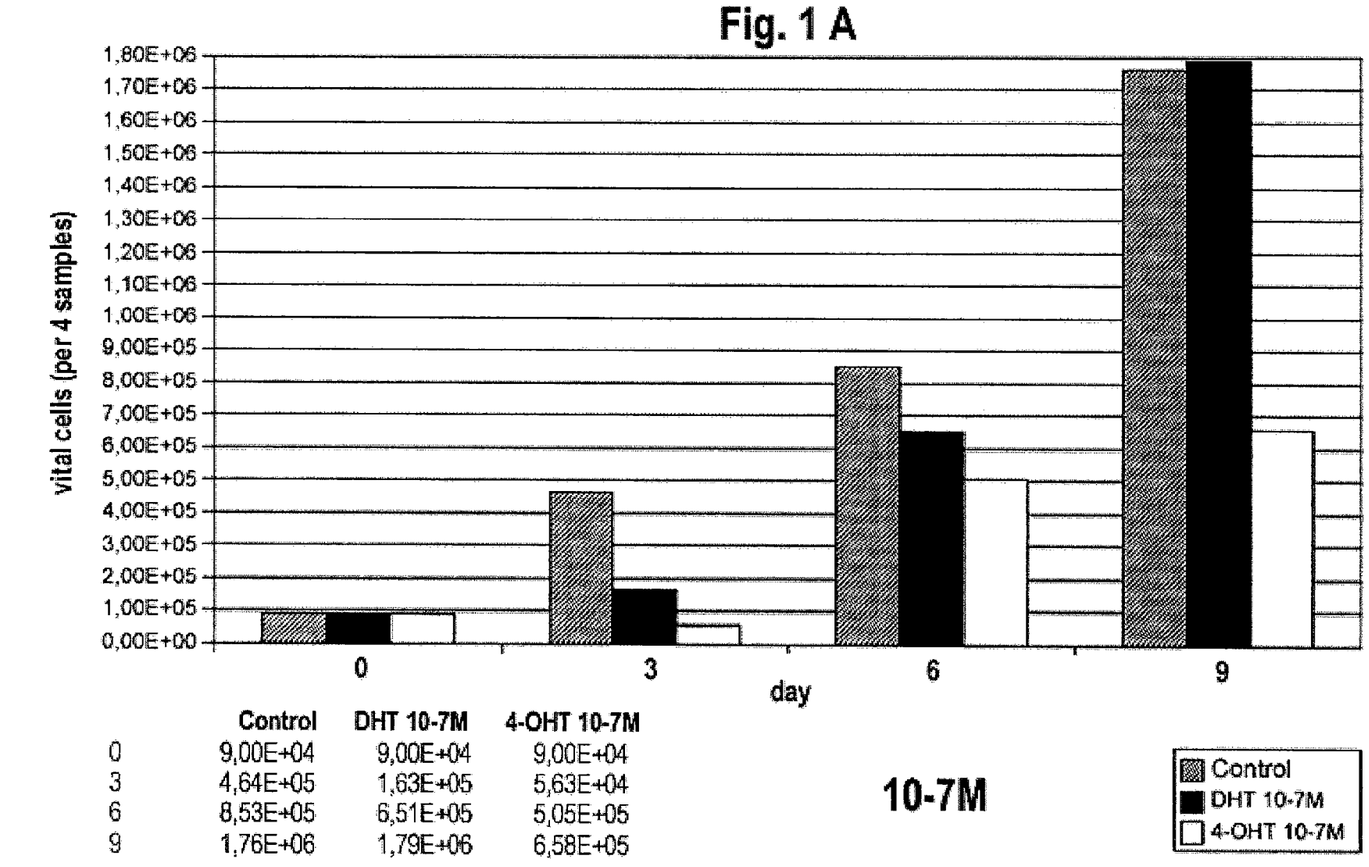
FIG. 1A shows results on an inhibition of MCF-7 cell proliferation for a compound at concentrations of $10^{-7}$ M of DHT and separately 4-OHT, and a comparison with a control.
FIG. 1B shows results on an inhibition of MCF-7 cell proliferation for a compound at concentrations of $10^{-8}$ M of DHT and separately 4-OHT, and a comparison with a control.
FIG. 1C shows results on an inhibition of MCF-7 cell proliferation for a compound at concentrations of $10^{-9}$ M of DHT and separately 4-OHT, and a comparison with a control.
Figure 1C:
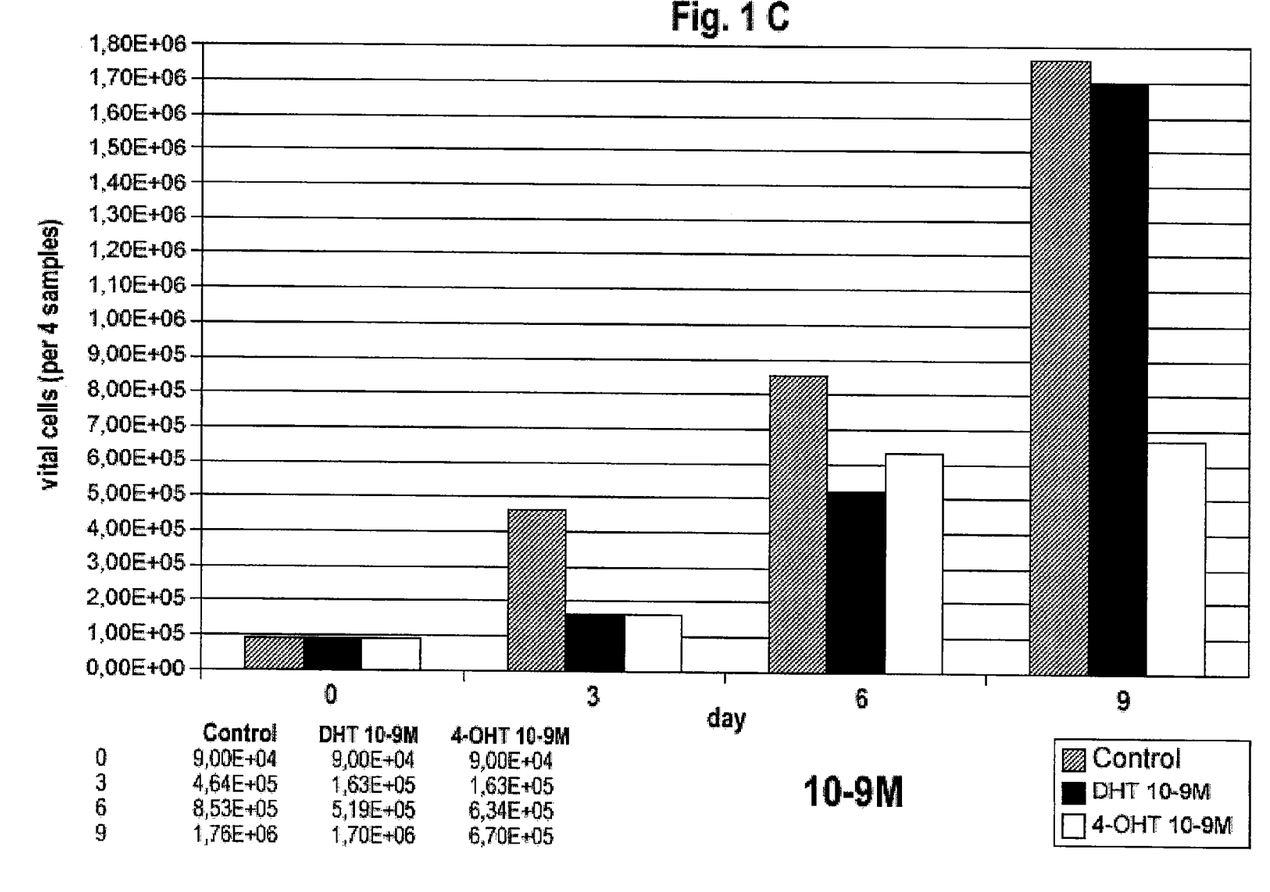

The results on an inhibition of MCF-7 cell proliferation are shown in FIGS. 1A, 1B and 1C for the compound concentrations of $10^{-7}$ M, $10^{-8}$ M and $10^{-9}$ M of either DHT or 4-OHT, respectively, and compared with the control. The results demonstrate a significantly enhanced inhibitory effect on MCF-7 cell proliferation in case of using the compound 4-hydroxytestosterone according to the present invention, significantly stronger than 4-dihydrotestosterone and particularly stronger than the control.

The surprisingly enhanced efficacy of 4-OHT compared to DHT can be explained by the effects, that 4-OHT can specifically bind strongly to the androgen receptor (AR) and eliciting anabolic/apoptotic effects rather than androgenic effects. DHT on the other hand preferentially evokes androgenic effects.

Example 8

Double blind clinical tests were conducted with a group of 10 female patients. In this clinical testing, particular attention was paid to hormone receptor statuses of patients' target breast cancer tissue regarding progesterone receptor (PR) and in particular regarding estrogen receptor (ER); The cancers of the patients were assumed to be predominantly androgen receptor (AR) positive. Among this group, six patients had histologically ascertained malign breast carcinoma (C. mammae). The tumors of 5 patients of this investigated sub-group were found to be progesteron receptor (PR) negative and, in particular, estrogen receptor (ER) negative (status level 0 (zero)). With respect to Her-2-neu, three patients did show a negative status, one had a moderate (level 1) and another had a strong (level 2) receptor status. In a sixth patient, the presence of a malign breast carcinoma was ascertained, but the amount of cancer tissue was too low to determine receptor status.

The remaining four patients did not show a malign disease, but appeared as having normal or mastopathic breast tissue.

All 10 female patients were topically and locally treated using 4-hydroxytestosterone as active agent, by administering of a cream as described in Example 2 locally to target skin portions of the breasts. After continuing daily topical administration once a day during an administration period of 3 months, clinical investigations on therapeutic effects were performed.

The results of the 6 patients having malign breast carcinoma are shown in the following Table 1, together with the receptor status determined for patient nos. 1 to 5.

| Patient No. | Age | ER | PR | Her2neu | Clinical Remission |
|---|---|---|---|---|---|
| # 1 | 62 yrs. | 0 | 0 | 0 | yes |
| # 2 | 54 yrs. | 0 | 0 | 1 | pending |
| # 3 | 87 yrs. | 0 | 0 | 0 | yes |
| # 4 | 68 yrs. | 0 | 0 | 2 | pending |
| # 5 | 57 yrs. | 0 | 0 | 0 | pending |
| # 6 | 50 yrs. | Ø | Ø | Ø | yes |

Among those women so far subjected to post-treatment investigations, three patients did show a noticeable remission of breast cancer tissues as determined by mammography.

Though receptor status of the tumor of the sixth patient of this cancer sub-group is unknown, there was also a clear clinical remission ascertained in this case.

With respect to the remaining 4 patients having non-malign disease states, it is to be noted that there is a clear tendency for tissue reduction of the apparently normal or mastopathic appearing tissues in the course of topical administration.

The results of this clinical study show two main important effects of the pharmaceutical composition according to the present invention comprising 4-hydroxytestosterone (4-OHT). Firstly, 4-OHT shows an excellent efficacy in shrinking cancerous tissues. Secondly, and still more surprisingly, even ER negative cancer cells can be effectively treated.

Taken together, the findings made in the present invention support the concept that 4-OHT can efficiently act via the AR, and that apoptosis can eventually be realized.

The findings of the present invention thereby make valuable therapeutic and/or prophylactic treatments feasible. Among other useful applications including adjuvant therapy, neoadjuvant therapy is of particular importance by making use of the substantial reduction of tumour volume to assist or enable subsequent surgical treatment schemes.

Example 9

A 42 years old patient with bilateral breast-cancer and skin metastases after surgery was treated daily with a cream corresponding to example 2. After 4 weeks of treatment the skin metastases have disappeared.

Example 10

A 50 years old patient with large breast cancer (diameter: 12 cm) massive tumour-spread and metastatic liver disease was treated by partial tumour-resection and subsequent daily application of a cream corresponding to example 2. The patient exhibited under treatment no further tumour growth and even a reduction of nonresectable tumour-mass.

Example 11

A 74 years old patient with advanced breast cancer and tumour-spread to the lymphatics was treated daily for 10 weeks. A substantial reduction of tumour volume occurred and in the affected lymph nodes no tumour cells were present anymore.

The invention claimed is:

1. A method of treatment of breast cancer, the method comprising steps of:
    (a) providing 4,17β-dihydroxyandrost-4-ene-3-one, a salt thereof, or an ester thereof in an amount effective for such treatment; and
    (b) administering to females in need of such treatment the effective amount of 4,17β-dihydroxyandrost-4-ene-3-one, a salt thereof, or an ester thereof,
    wherein 4,17β-dihydroxyandrost-4-ene-3-one, a salt thereof, or an ester thereof is an androgen receptor specific compound that binds to an androgen receptor, and wherein 4,17β-dihydroxyandrost-4-ene-3-one, a salt thereof, or an ester thereof elicits anabolic/apoptotic properties rather than androgenic properties.

2. The method according to claim 1, wherein the breast cancer is ductal, medullary or lobular breast carcinoma.

3. The method according to claim 1, wherein the effective amount of 4,17β-dihydroxyandrost-4-ene-3-one, a salt thereof, or an ester thereof is administered together with an effective amount of one or more additional components selected from the group consisting of an estrogen-receptor antagonist, an aromatase inhibitor, a cytostatic and antibodies against Her2neu.

4. The method according to claim 1, wherein the administration is topical.

* * * * *